US009763838B2

(12) United States Patent
Piccolo-Wignall et al.

(10) Patent No.: US 9,763,838 B2
(45) Date of Patent: Sep. 19, 2017

(54) SPINE BOARD WITH INTERIOR CHANNELS (71) Applicant: Rx 1186, LLC, Fairfield, CA (US)

(72) Inventors: John Piccolo-Wignall, Fairfield, CA (US); Douglas C. Fritz, Napa, CA (US); James R. Osborn, Richmond, CA (US)

(73) Assignee: Rx 1186, LLC, Fairfield, CA (US)

( * ) Notice: Subject to any disclaimer, the term of this patent is extended or adjusted under 35 U.S.C. 154(b) by 0 days.

(21) Appl. No.: 14/792,981

(22) Filed: Jul. 7, 2015

(65) Prior Publication Data

US 2016/0008190 A1    Jan. 14, 2016

Related U.S. Application Data

(60) Provisional application No. 62/022,308, filed on Jul. 9, 2014.

(51) Int. Cl.
*A61G 1/044* (2006.01)
*A61G 1/04* (2006.01)
(Continued)

(52) U.S. Cl.
CPC ............ *A61G 1/044* (2013.01); *A61F 5/3761* (2013.01); *A61G 1/04* (2013.01); *A61G 1/048* (2013.01); *A61G 7/1084* (2013.01)

(58) Field of Classification Search
CPC ...... A61F 5/055; A61F 5/05883; A61F 5/058; A61F 5/3707; A61F 5/37; A61F 5/3776; A61F 5/3761; A61F 2/7843; A61F 2/7812; A61F 2/80; A61F 13/06; A61F 2002/30507; A61F 2002/30563; A61F 2002/30579; A61F 2002/30878; A61F 2002/347; A61F 2002/3491; A61F 2002/3496; A61F 2002/4085;
(Continued)

(56) References Cited

U.S. PATENT DOCUMENTS 3,449,776 A    6/1969   Brock
4,267,830 A    5/1981   Vick
(Continued)

FOREIGN PATENT DOCUMENTS

WO    WO 86/07253    * 12/1986

OTHER PUBLICATIONS

International Search Report mailed Nov. 6, 2015 for corresponding International Application No. PCT/US2015/039481 filed Jul. 8, 2015, 5 pages.
(Continued)

*Primary Examiner* — Kari Rodriquez
(74) *Attorney, Agent, or Firm* — Leanna Taveggia Farrell; Westman, Champlin & Koehler, P.C.

(57) ABSTRACT

A spine board includes a main body having a top surface and an opposing bottom surface that define a thickness of the main body, a first end and an opposing second end that define a length of the main body and a first longitudinal side and a second longitudinal side that define a width of the main body. Longitudinal and lateral channels are located between the top and bottom surfaces in the main body and contain either cartridges that house straps for securing the patient to the board or a key to affix a cervical collar to the main body.

17 Claims, 12 Drawing Sheets

(51) Int. Cl.
*A61F 5/37* (2006.01)
*A61G 1/048* (2006.01)
*A61G 7/10* (2006.01)

(58) Field of Classification Search
CPC ......... A61F 5/3769; A61G 1/04; A61G 1/044;
A61G 1/048; A61G 7/1084; A61G 1/01;
A61G 7/072; A61G 1/00; A61G 1/013;
A61G 1/02; A61G 1/0206; A61G 1/0287;
A61G 7/0504; A61G 2200/14; A61G
2200/54; A61G 5/05883; A61B 6/04
USPC .............................. 128/869, 870; 5/625–630
See application file for complete search history.

(56) References Cited

U.S. PATENT DOCUMENTS

| | | | |
|---|---|---|---|
| 4,473,912 A | 10/1984 | Scheidel et al. | |
| 4,506,664 A | 3/1985 | Brault | |
| 4,736,474 A | 4/1988 | Moran et al. | |
| 4,895,173 A | 1/1990 | Brault et al. | |
| 4,945,583 A | 8/1990 | Schnitzler | |
| 5,121,514 A * | 6/1992 | Rosane | A61G 1/01 128/870 |
| 5,121,756 A | 6/1992 | Koledin | |
| 5,334,133 A | 8/1994 | Carroll | |
| 5,433,741 A | 7/1995 | Truglio | |
| 5,839,137 A * | 11/1998 | Butler | A61G 1/01 5/620 |
| 5,865,780 A | 2/1999 | Tuite | |
| 6,055,988 A | 5/2000 | Perisho | |
| D479,878 S | 9/2003 | Phillips et al. | |
| D511,835 S | 11/2005 | Holland | |
| 6,966,321 B2 * | 11/2005 | Hess | A61F 5/3707 128/846 |
| 7,055,199 B2 | 6/2006 | Thompson | |
| 7,120,954 B2 | 10/2006 | Traut et al. | |
| 7,165,278 B2 | 1/2007 | Tomcany et al. | |
| 7,360,264 B2 | 4/2008 | Tomcany | |
| 7,426,761 B2 | 9/2008 | Tomcany et al. | |
| 7,437,789 B2 | 10/2008 | Thompson | |
| 2011/0185504 A1 * | 8/2011 | Kenalty | A61G 1/00 5/626 |
| 2012/0102650 A1 | 5/2012 | McGlynn | |
| 2014/0068865 A1 | 3/2014 | Heck | |

OTHER PUBLICATIONS

International Search Report and Written Opinion mailed Jan. 28, 2016 for corresponding International Application No. PCT/US2015/039481 filed Jul. 8, 2015, 15 pages.

* cited by examiner

SPINE BOARD WITH INTERIOR CHANNELS

CROSS REFERENCE TO RELATED APPLICATION

The present application is based on and claims the benefit of U.S. provisional patent application Ser. No. 62/022,308, filed Jul. 9, 2014, the content of which is hereby incorporated by reference in its entirety.

BACKGROUND

Spine boards are patient handling devices that provide rigid support to prevent further injury of a patient while the patient is being transported to a medical center for treatment. They are commonly used by medical personnel during emergency and rescue situations so as to provide increased efficiency and effectiveness in performing the vital tasks required.

The discussion above is merely provided for general background information and is not intended to be used as an aid in determining the scope of the claimed subject matter.

SUMMARY

A spine board includes a main body having a top surface and an opposing bottom surface that define a thickness of the main body, a first end and an opposing second end that define a length of the main body and a first longitudinal side and an opposing second longitudinal side that define a width of the main body. The first and second longitudinal sides connect the first end to the second end. A plurality of longitudinal channels extend longitudinally within the main body. Each longitudinal channel is defined at least by an open first end and an open second end. The open first end intersects with the first end of the main body and the open second end intersects with the top surface of the main body. The spine board also includes a plurality of longitudinal cartridges each containing a longitudinal strap and each being removably inserted into one of the plurality of longitudinal channels. The longitudinal cartridges each have a leading end that is located at the open second end of the longitudinal channel when placed in the longitudinal channel and a trailing end that is located at the open first end of the longitudinal channel when placed in the longitudinal channel and locks the longitudinal cartridge to the main body.

A spine board includes a main body having a top surface and an opposing bottom surface that define a thickness of the main body, a first end and an opposing second end that define a length of the main body and a first longitudinal side and an opposing second longitudinal side that define a width of the main body. The first and second longitudinal sides connect the first end to the second end. A plurality of lateral channels extend laterally within the main body and are defined at least by open first ends and open second ends. Each open first end intersects with the first longitudinal side of the main body and each open second end intersects with the second longitudinal side of the main body. The spine board also includes plurality of lateral cartridges each containing a lateral strap and each being removably inserted into one of the plurality of lateral channels. The lateral cartridges each have a leading end that is located at the open first ends of the lateral channels when placed in the lateral channels and a trailing end that is located at the open second ends of the lateral channels when placed in the lateral channels. The trailing end lock the lateral cartridge to the main body.

A method of securing a patient to a spine board includes providing a main body of the spine board having a top surface and an opposing bottom surface that defines a thickness of the main body, a first end and an opposing second end that defines a length of the main body and a first longitudinal side and a second longitudinal side that defines a width of the main body. A longitudinal strap is pulled from a longitudinal cartridge located in a longitudinal channel in the main body, wherein the longitudinal channel is located between the top and bottom surfaces, extends longitudinally for less than the length of the main body and has an open first end and an open second end. The longitudinal strap is secured over a patient using hook and loop material that comprises the longitudinal strap.

A mechanism for securing a cervical collar to a spine board is also described. A collar stabilization key has a leading end and a trailing end. The collar stabilization key is inserted into a longitudinal channel located within a main body of the spine board and has a first end that intersects with a first end of the main body and a second end that intersects with a top surface of the main body. The leading end of the collar stabilization key mates with a post coupled to a cervical collar so as to secure the cervical collar to the main body of the spine board and the trailing end of the collar stabilization key locks the collar stabilization key in the longitudinal channel and to the main body.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The claimed subject matter is not limited to implementations that solve any or all disadvantages noted in the background.

DETAILED DESCRIPTION

The following embodiments describe a support article or spine board that provides increased efficiency and effectiveness in performing the vital tasks required by medical personnel in treating patients who have sustained physical injury. The support article or spine board includes an adjustable brace or cervical collar that can be fitted around the patient's neck before being positioned and locked into the board and preloaded straps in cartridges located in channels within the main body of the board. Together these components provide medical personnel with the ability to secure and constrain patients during transport so as to prevent further injury as well as provide medical personnel with the ability to apply preventative treatments immediately so as to limit the severity of injury.

Figure 1:
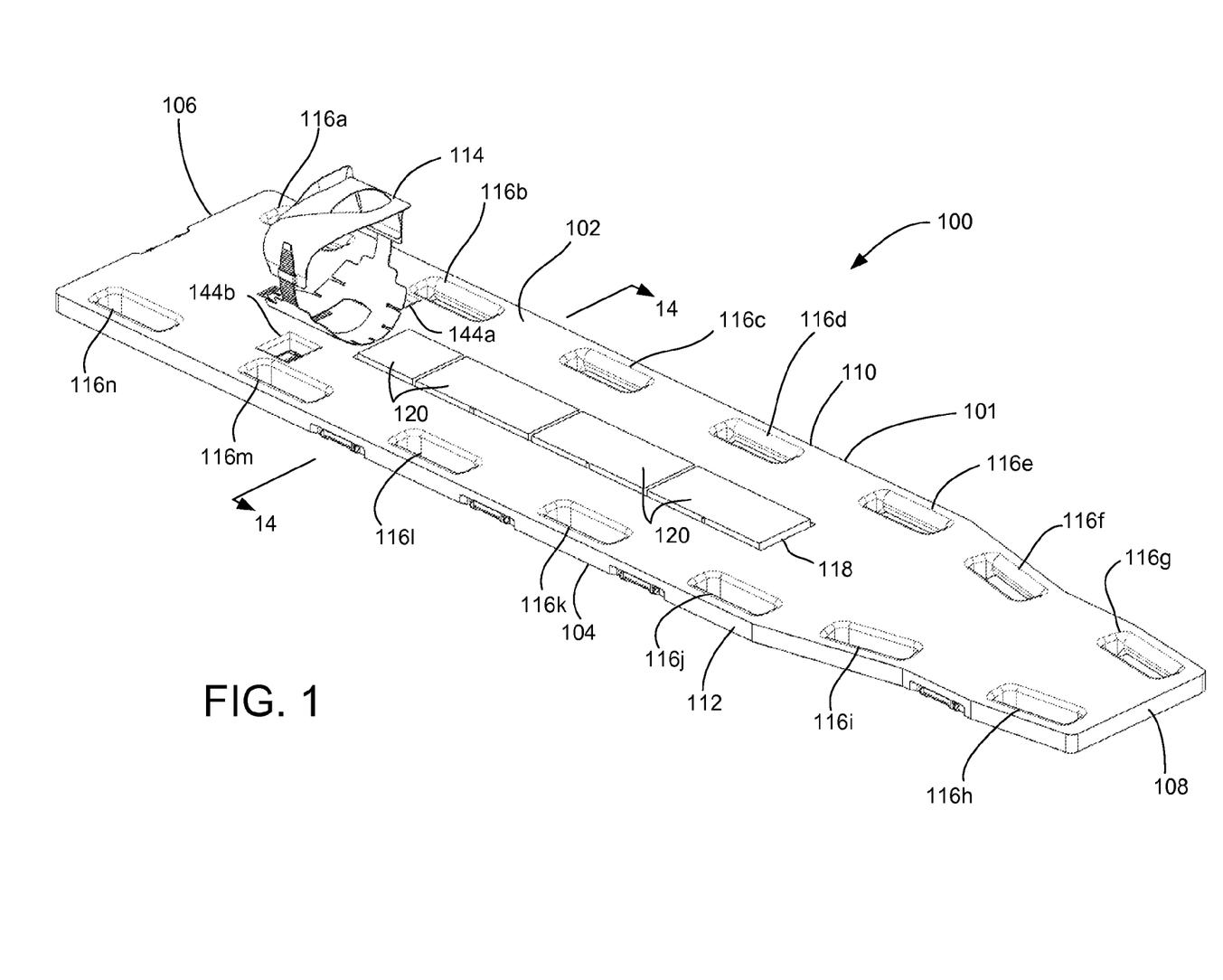
FIG. 1 is a perspective view illustrating a spine board and a cervical collar mounted to the spine board according to one embodiment.

FIG. 1 is a perspective view of a support article or spine board 100. FIGS. 2-7 are a top view, a bottom view, a right side view, a left side view, a back view and a front view of spine board 100. Board 100 includes and contains multiple features that are required to treat patients at the scene of an emergency by first responders and allows for the most efficient use of those features to drastically reduce the amount of critical time needed to prepare the injured person for transport to a medical facility. Board 100 and its multiple features is easily cleaned, has intuitive use, limited parts and is equipped with replaceable components.

Spine board 100 includes a main body 101 having a top surface 102, an opposing bottom surface 104, a first end 106, an opposing second end 108, a first longitudinal side 110 and an opposing second longitudinal side 112. The distance between top surface 102 and bottom surface 104 defines a thickness 127 (FIG. 6) of main body 101. The distance between first end 106 and second end 108 defines a length 123 (FIG. 2) of main body 101. The distance between first longitudinal side 110 and second longitudinal side 112 defines a width 125 (FIG. 6) of main body 101. First and second longitudinal sides 110 and 112 connect first and second ends 106 and 108. In one embodiment, spine board 100 is made of a light-weight synthetic material, durable enough to withstand years of use by medical personnel.

Spine board 100 includes an adjustable brace or cervical collar 114 mounted to main body 101 that protrudes from top surface 102, a plurality of grasping handles 116a-n and an ice tray 118. Cervical collar 114 is fitted around a patient's neck and then fixed to board 100 prior to patient transport to prevent as much movement of the spine as possible. A collar stabilization key 136 (FIGS. 2-3 and 6) is located internal to main body 101 of board 100 and is used to hold the cervical collar 114 in place and prevent motion of the head and neck in multiple directions. Cervical collar 114 and collar stabilization key 136 will be discussed in more detail below.

Handles 116a-n are spaced apart from each other and are placed in locations adjacent to and along first longitudinal side 110 and second longitudinal side 112 to allow medical personnel to carry spine board 100. Along the mid-section of main body 101 of board 100 is ice tray 118 that is recessed from top surface 102 of main body 101 and, in one embodiment, is configured to receive ready-to-use chemically activated cold packs 120, which can be activated if the patient requires such treatment along the back. These can be utilized at the discretion of the emergency responder if the patient requires such treatment for their injuries. Recessed ice tray 118 holds the cold packs 120 in place. In one embodiment, the top surfaces of cold packs 120 may protrude from top surface 102 of main body 101 and, in another embodiment, can be held in place with hook and loop material.

Also incorporated into the board are a plurality of channels and a plurality of cartridges that are inserted in the channels and contain straps. The channels exist within main body 101 and are located interior to the outer surfaces of board 100 including between top surface 102 and bottom surface 104 and between first end 106 and second end 108 and between first longitudinal side 110 and second longitudinal side 112. The channels provide openings to receive the cartridges, which contain the straps that secure the patient to the board. The cartridges are single use units that are loaded and stored within the board and provide easy access to the straps when needed for treatment of the patient.

Figure 2:
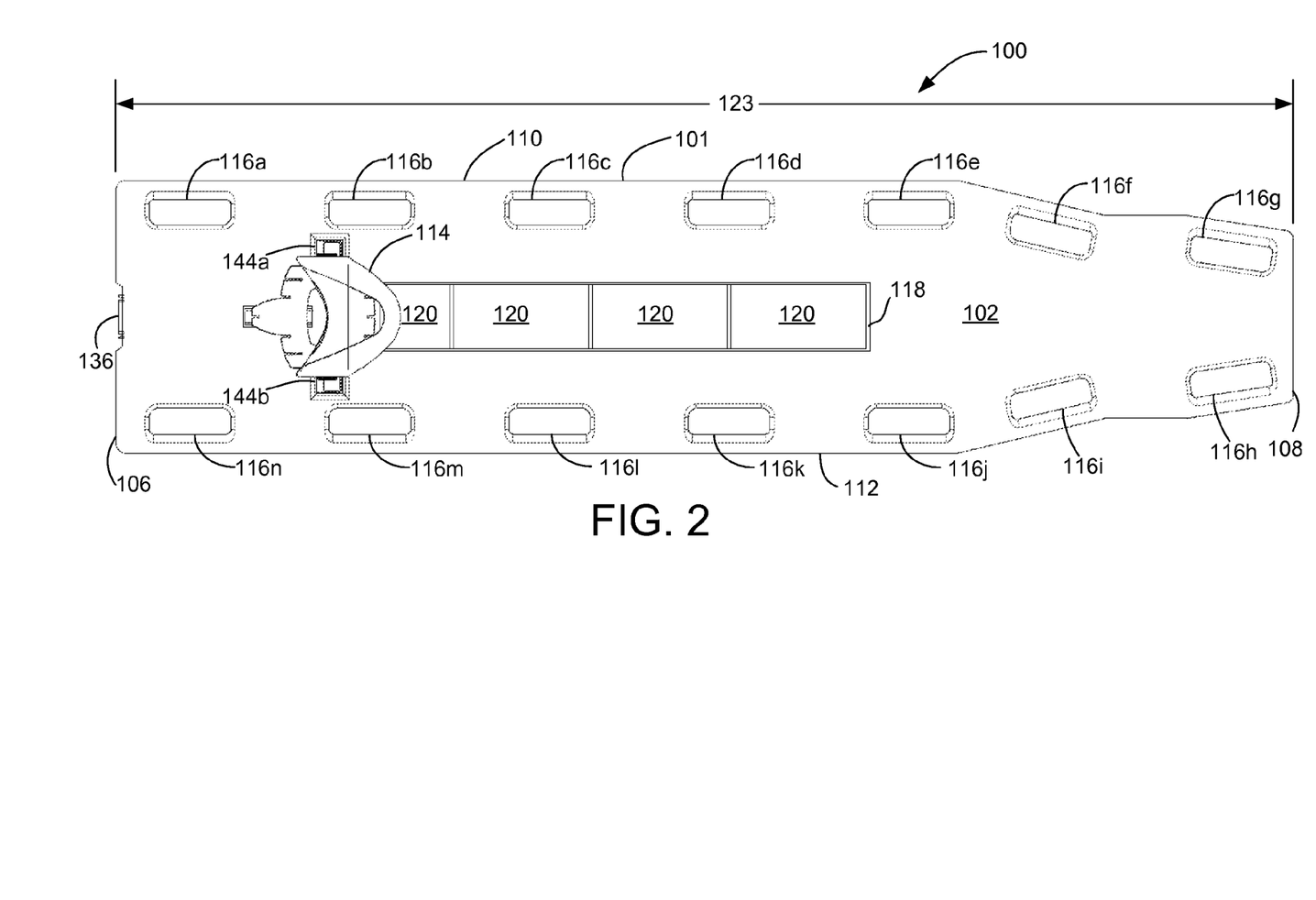
FIG. 2 is a top view of FIG. 1.
Figure 3:
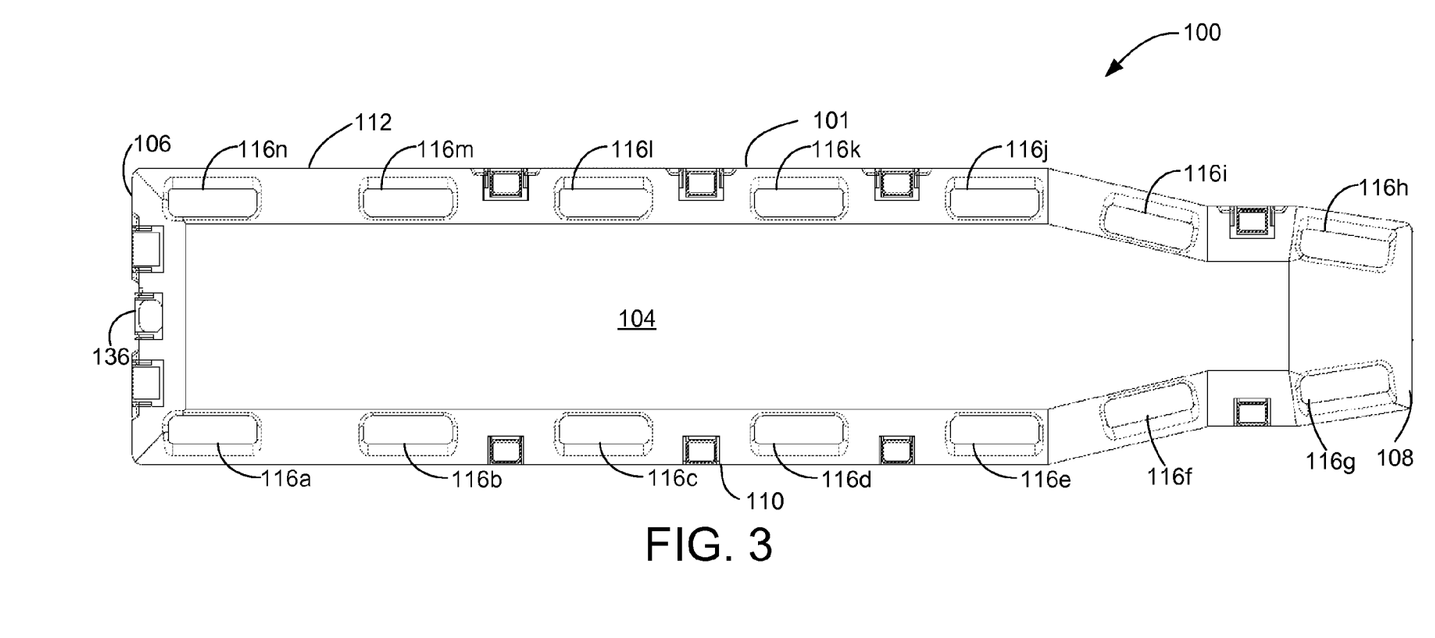
FIG. 3 is a bottom view of FIG. 1.
Figure 4:
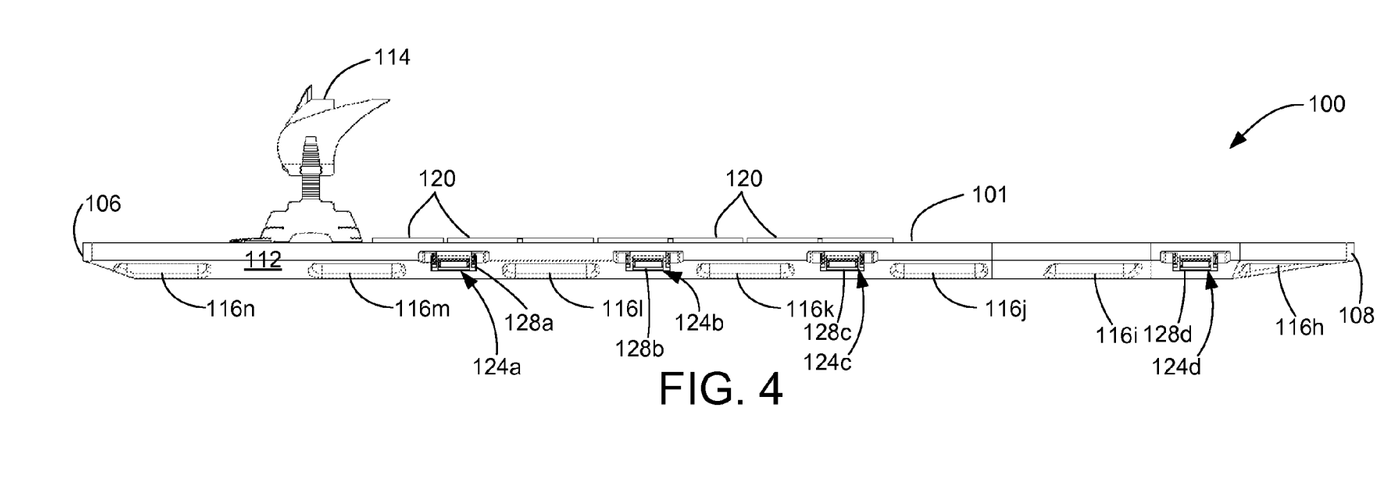
FIG. 4 is a right side view of FIG. 1.
Figure 5:
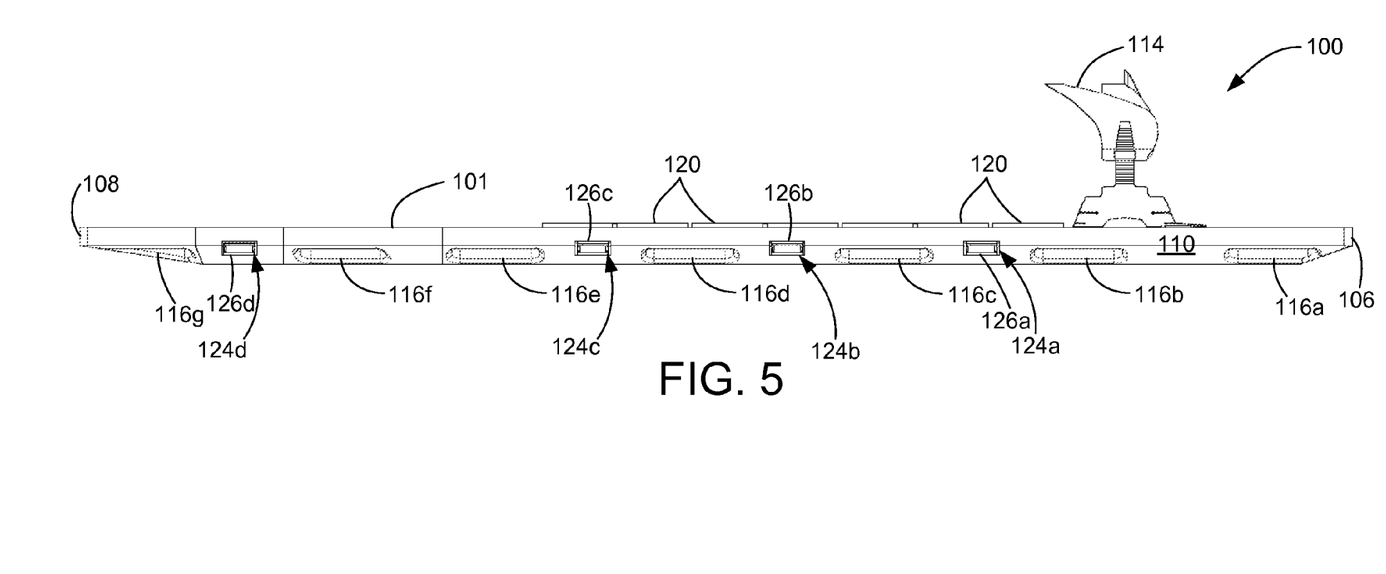
FIG. 5 is a left side view of FIG. 1.
Figure 6:
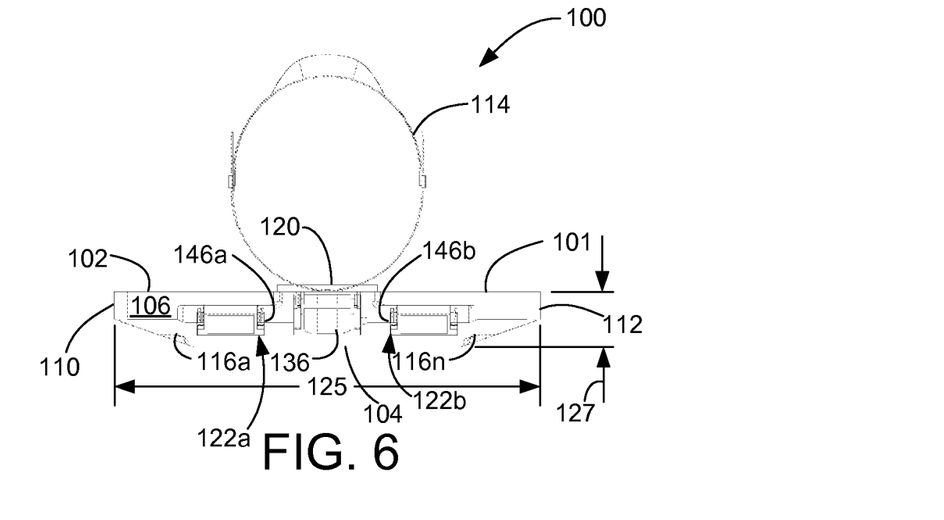
FIG. 6 is a back view of FIG. 1.
Figure 7:
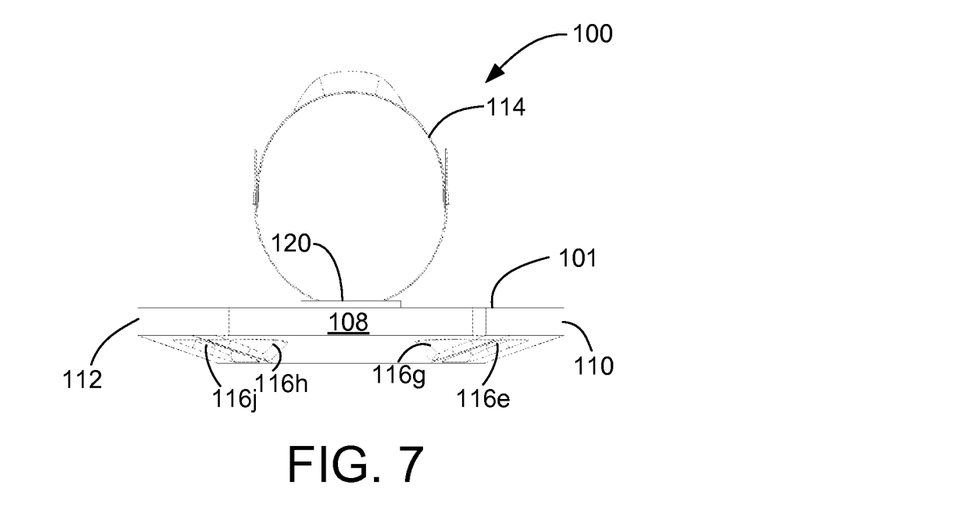
FIG. 7 is a front view of FIG. 1.

In one embodiment, there are two different types of channels that exist within main body 101 of board 100. First, a pair of longitudinal channels 122a-b (FIG. 6 and better shown in FIG. 8) that extend longitudinally along a portion of length 123 of spine board 100 (i.e., along either side of cervical collar 114) from first end 106 to second ends 144a and 144b (FIGS. 1 and 2). Second, a plurality of lateral channels 124a-d (FIGS. 4 and 5) that extend laterally through width 125 of main body 101 from first longitudinal side 110 to second longitudinal side 112.

Figure 8:
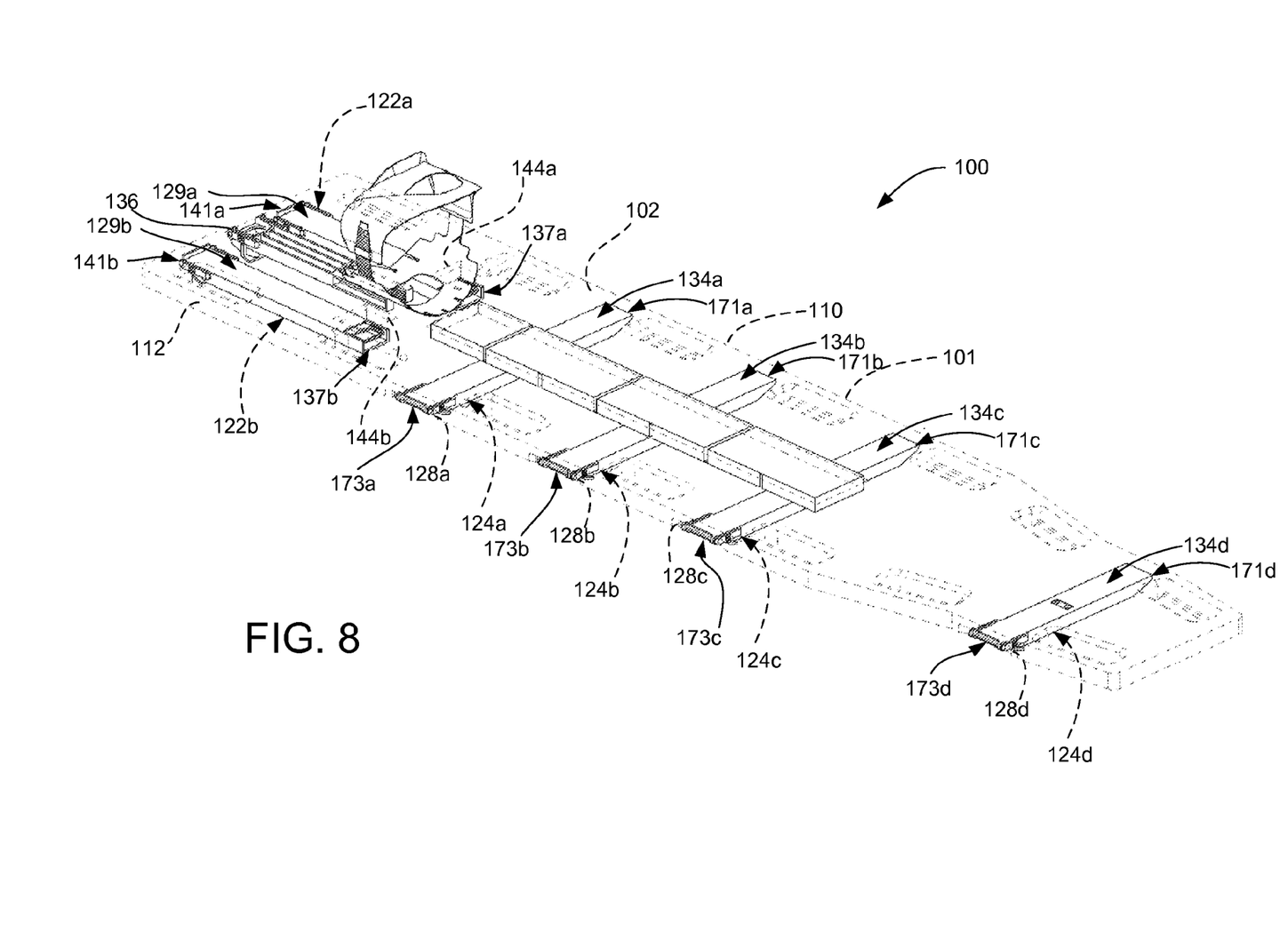
FIG. 8 is the perspective view illustrated in FIG. 1 with the spine board shown in phantom to illustrate internal components.

FIG. 8 is the perspective view of spine board 100 in FIG. 1 with main body 101 shown in phantom to illustrate internal components. Longitudinal channels 122a and 122b are located inside main body 101 between top surface 102 and bottom surface 104 and have open second ends or exit ends 144a and 144b, respectively, and open first ends or insertion ends 146a and 146b (FIG. 6), respectively. Open first ends 146a and 146b intersect with first end 106 of main body 101 and serve as the insertion openings into channels 122a-b for cartridges 129a and 129b. Open second ends 144a and 144b intersect with top surface 102 of main body 100 and serve as exit ends for straps stored in cartridges 129a and 129b. First longitudinal channel 122a and second longitudinal channel 122b are spaced apart from first and second longitudinal sides 110 and 112 of main body 101 and from each other. First longitudinal channel 122a is located in closer proximity to first longitudinal side 110 than second longitudinal side 112. Second longitudinal channel 122b is located in closer proximity to second longitudinal side 112 than first longitudinal side 110. Longitudinal channels 122a and 122b extend for a length from first end 106 of main body 101 to open second ends 144a and 144b, which are in an area proximal to where cervical collar 114 is attached to main body 101.

Lateral channels 124a, 124b, 124c and 124d are oriented substantially perpendicular to longitudinal channels 122a-b, but do not intersect longitudinal channels 122a-b since they are spaced away from longitudinal channels 122a-b. Lateral channels 124a-d are also located inside main body 101 between and spaced apart from top surface 102 and bottom surface 104, have a length that is a width of main body 101, are spaced apart from each other along length 123 of main body 101 and have open first ends 126a, 126b, 126c and 126*d* that intersect with first longitudinal side 110 and open second ends 128*a*, 128*b*, 128*c* and 128*d* that intersect with second longitudinal side 112. Both open first ends 126*a-d* and open second ends 128*a-d* serve as exit ends for straps stored in cartridges 134*a-d*.

As illustrated and as previously discussed, longitudinal channels 122*a-b* and lateral channels 124*a-d* that exist within main body 101 of spine board 100 house and store removable cartridges that contain straps. Longitudinal channels 122*a-b* receive and house first and second longitudinal cartridges 129*a* and 129*b* having leading ends 137*a* and 137*b* and trailing ends 141*a* and 141*b*, respectively. Lateral channels 124*a-d* receive and house lateral cartridges 134*a*, 134*b*, 134*c* and 134*d* having leading ends 171*a-d* and trailing ends 173*a-d*, respectively. Each cartridge 129*a-b* and 134*a-d* contain and store a strap used to secure the patient to main body 101 of board 100. The straps are made with hook and loop material for securing via attachment onto themselves.

Figures 9, 10:
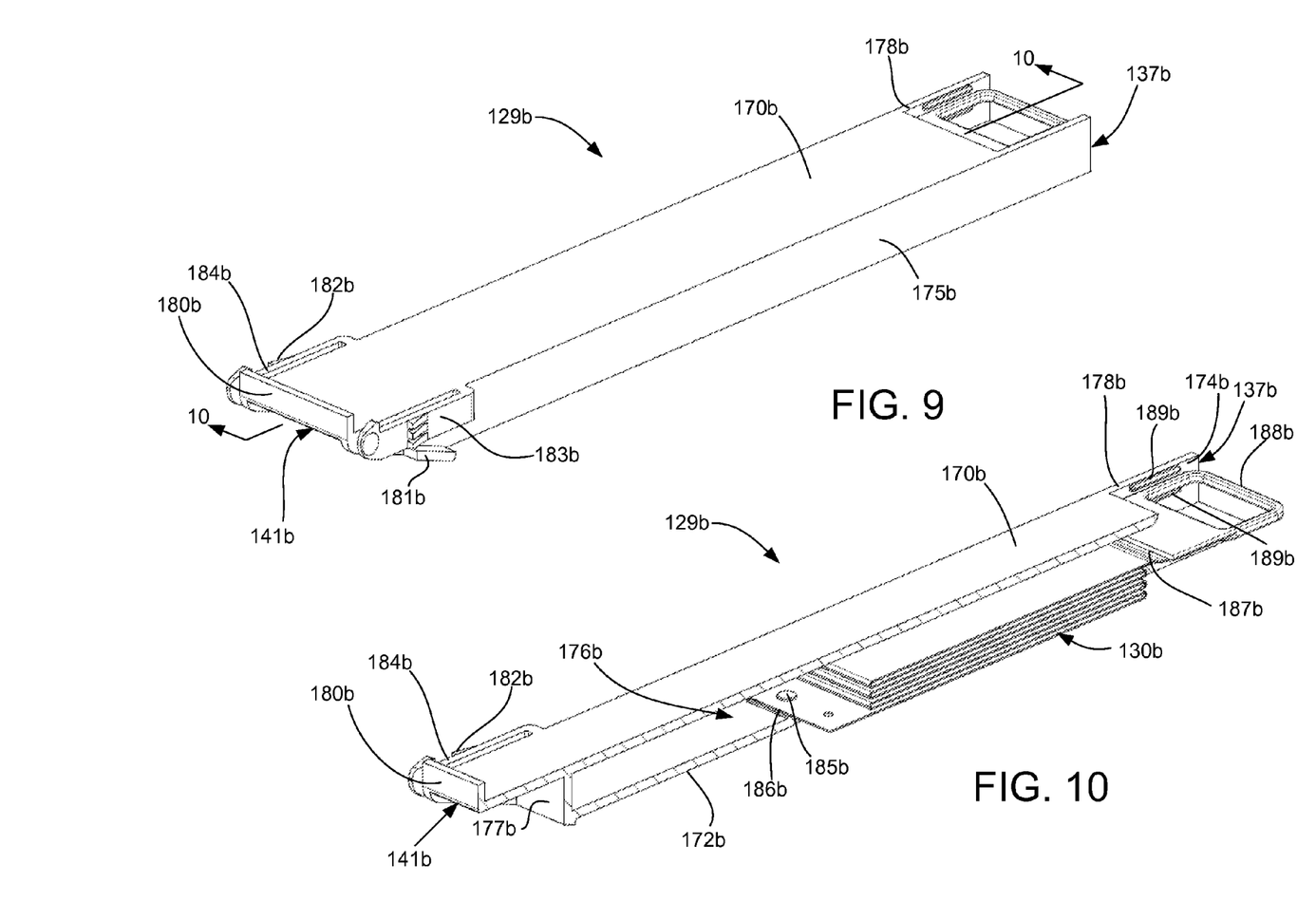
FIG. 9 is a perspective view of an exemplary longitudinal cartridge that is to be located in an exemplary longitudinal channel in the spine board according to one embodiment.
FIG. 10 is a perspective section view of the exemplary longitudinal cartridge in FIG. 9 taken through the line indicated in FIG. 9 and illustrating a strap housed by the exemplary longitudinal cartridge according to one embodiment.

FIG. 9 is a perspective view of exemplary longitudinal cartridge 129*b* that is to be removably inserted in exemplary longitudinal channel 122*b* according to one embodiment. FIG. 10 is a perspective section view of exemplary longitudinal cartridge 129*b* taken through the line indicated in FIG. 9 to show strap 130*b* housed and stored in exemplary cartridge 129*b* according to one embodiment. Exemplary longitudinal cartridge 129*b* is substantially identical to longitudinal cartridge 129*a*, which is located in longitudinal channel 122*a*, so features described with respect to cartridge 129*b* should be applied to cartridge 129*a*.

As previously discussed, longitudinal cartridge 129*b* includes a leading end 137*b* and a trailing end 141*b*. When placed in longitudinal channel 122*b*, leading end 137*b* is located at open second end 144*b* and trailing end 141*b* is located at open second end 146*b*. Trailing end 141*b* includes flanges 180*b*, 181*b* and 182*b* (substantially identical to flange 181*b*) and a pair of substantially identical spring or barbed clips 183*b* and 184*b*. Flanges 180*b*, 181*b* and 182*b* and spring clips 183*b* and 184*b* engage with recesses in main body 101 for locking longitudinal cartridge 129*b* into channel 122*b* of main body 101. Longitudinal cartridge 129*b* further includes a top wall 170*b*, a bottom wall 172*b*, a first side wall 174*b* and a second side wall 175*b*. Together, top wall 170*b*, bottom wall 172*b*, first side wall 174*b* and second side wall 175*b* define a compartment 176*b* for containing and storing strap 130*b*. Compartment 176*b* is also defined between a trailing end wall 177*b* located proximal to trailing end 141*b* of longitudinal cartridge 129*b* and an opening 178*b* in leading end 137*b* of longitudinal cartridge 129*b*. Opening 178*b* provides access to strap 130*b* and aligns with second end 144*b* of channel 122*b* in main body 101 of board 100.

As illustrated in FIG. 10, strap 130*b* is stored in cartridge 129*b* in a single serpentine arrangement of hook and loop strap material (i.e., strap 130*b* is folded over and onto itself) and is secured to bottom wall 172*b* of compartment 176*b* at a first end 186*b* of strap 130*b* with at least one fastener 185*b*, such as one more rivets. Second end 187*b* of strap 130 includes a finger hook 188*b*. Finger hook 188*b* is secured to the interior facing walls 174*b* and 175*b* of compartment 176*b* with ribs 189*b* so as to prevent accidental or premature removal of strap 130*b* from cartridge 129*b*. However, other ways of securing finger hook 188*b* to interior facing walls 174*b* and 175*b* are possible.

Figure 11:
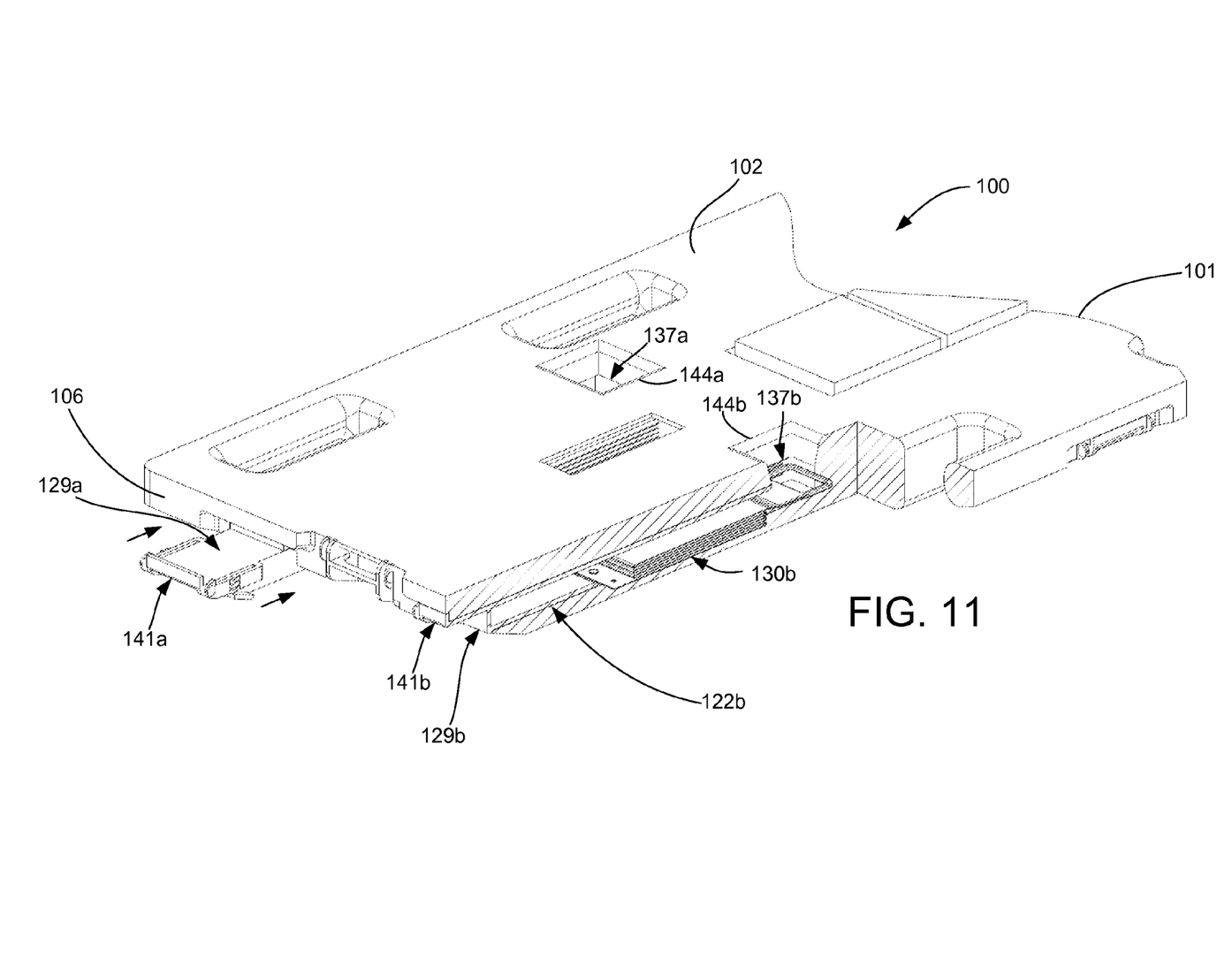
FIG. 11 is a partial perspective view of a section of the spine board illustrating the insertion of and placement of longitudinal cartridges in the main body of the spine board.

FIG. 11 is a partial perspective view of a section of spine board 100 illustrating the removable insertion of and placement of longitudinal cartridges 129*a* and 129*b* in main body 101 of spine board 100. As illustrated by longitudinal cartridge 129*a*, the leading ends 137*a* and 137*b* of the longitudinal cartridges 129*a* and 129*b* are inserted into channels 122*a* and 122*b*, respectively, at first end 106 of main body 101 and are slid along the lengths of channels 122*a* and 122*b* in the direction illustrated by the exemplary directional arrows until leading ends 137*a* and 137*b* reach second ends 144*a* and 144*b* of channels 122*a* and 122*b*. Second ends 144*a* and 144*b* of channels 122*a* and 122*b* are strap access cavities 144*a* and 144*b*, which are open to and communicate with top surface 102 of main body 101. As longitudinal cartridges 129*a* and 129*b* reach their full insertion position, the spring or barbed clips on trailing ends 141*a-b* will become compressed and as insertion is completed the spring or barbed clips will click into position, thereby indexing with main body 101 and holding cartridges 129*a-b* in place. The spring or barbed clips prevent the longitudinal cartridges 129*a* and 129*b* from being removed accidentally and additionally keep the longitudinal cartridges 129*a* and 129*b* in position as straps are removed for use on the patient.

The straps contained and stored in longitudinal cartridges 129*a* and 129*b*, such as a first longitudinal strap stored in first longitudinal cartridge 129*a* and a second longitudinal strap stored in second longitudinal cartridge 129*b*, are pulled from leading ends 137*a* and 137*b* and through strap access cavities 144*a* and 144*b* using the fingers hooks on the second ends of the straps, such as finger hook 188*b* of strap 130*b*. After the first longitudinal strap in longitudinal cartridge 129*a* is pulled out of cartridge 129*a* it is brought over a left shoulder of a patient and secured as described in detail below. After second longitudinal strap 130*b* in longitudinal cartridge 129*b* is pulled out of cartridge 129*b* it is brought over a right shoulder of the patient and secured as described in detail below. Therefore, the longitudinal straps stored in longitudinal cartridges 129*a* and 129*b* are used to secure the chest area of a patient by forming a cross shape across their chest after each strap is pulled out of each longitudinal cartridge 129*a-b* at exit ends 144*a* and 144*b* or strap access cavities 144*a* and 144*b*. In the alternative, the longitudinal straps do not necessarily have to cross the chest of the patient and can separately secure the right and left side of a patient's torso to the spine board. As illustrated and previously discussed, exit ends or strap access cavities 144*a* and 144*b* of longitudinal channels 122*a* and 122*b* are located in an area proximal cervical collar 114. The securing of the patient using the longitudinal straps will be discussed in more detail below.

Figures 12, 13:
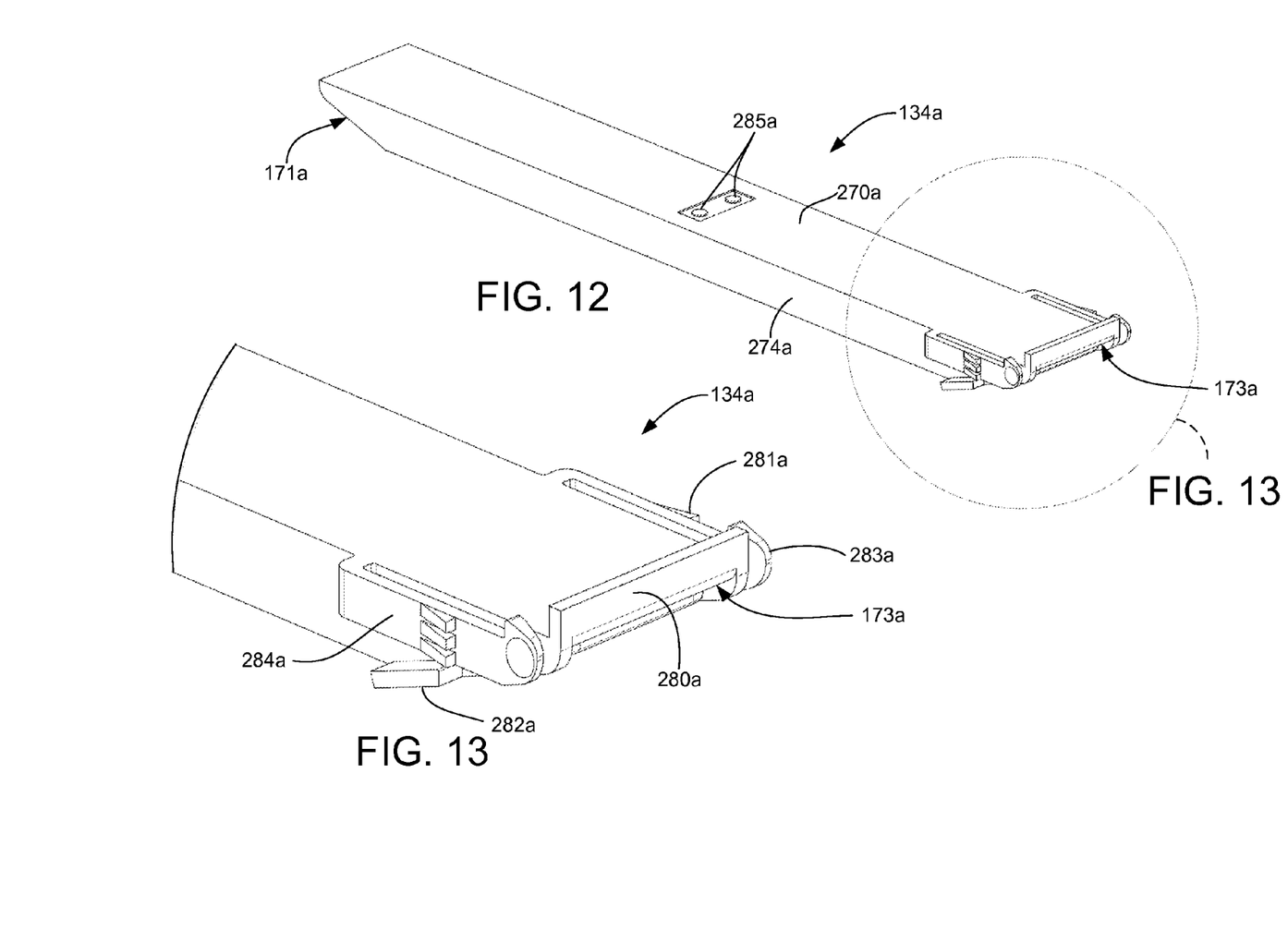
FIG. 12 is a perspective view of an exemplary lateral cartridge that is to be located in an exemplary lateral channel in the spine board according to one embodiment.
FIG. 13 is an enlarged view of the trailing end of the exemplary lateral cartridge illustrated in FIG. 12.

FIG. 12 is a perspective view of exemplary lateral cartridge 134*a* that is to be removably inserted in exemplary lateral channel 124*a* according to one embodiment. FIG. 13 illustrates an enlarged view of trailing end 173*a* of lateral cartridge 134*a* in FIG. 12. Exemplary lateral cartridge 134*a* is substantially identical to lateral cartridges 134*b* and 134*c* (FIG. 2) and is similar to lateral cartridge 134*d* (FIG. 2) in that the structure is substantially identical, but lateral cartridge 134*d* is shorter than lateral cartridges 134*a-c* because lateral channel 124*d* is shorter than lateral channels 124*a*, 124*b* and 124*c*. Still further, each hook and loop strap located in each lateral cartridge 134*a-c* are substantially identical, however, the hook and loop strap located in lateral cartridge 134*d* is shorter than the straps in lateral cartridges 134*a-c*. Therefore, features described with respect to cartridge 134*a* should also be applied to cartridges 134*b-d*.

As previously discussed, each lateral cartridge 134*a-d* includes leading end 171*a-d* and trailing end 173*a-d*. When placed in lateral channels 124*a-d*, leading end 171*a-d* are located at open first ends 126a-d and trailing ends 173a-d are located open second ends 128a-d. Each trailing end 173a-d includes flanges and a pair of substantially identical spring clips that engage with recesses in main body 101. As illustrated by the exemplary lateral cartridge 134a in FIGS. 12 and 13, trailing end 173a of lateral cartridge 134a includes flanges 280a, 281a and 282a (which is substantially identical to flange 281a) and pair of substantially identical spring clips 283a and 284a. Flanges 280a, 281a and 282a and spring clips 283a and 284a engage with recesses in main body 101 for locking lateral cartridge 134a into channel 124a of main body 101.

Figure 14:
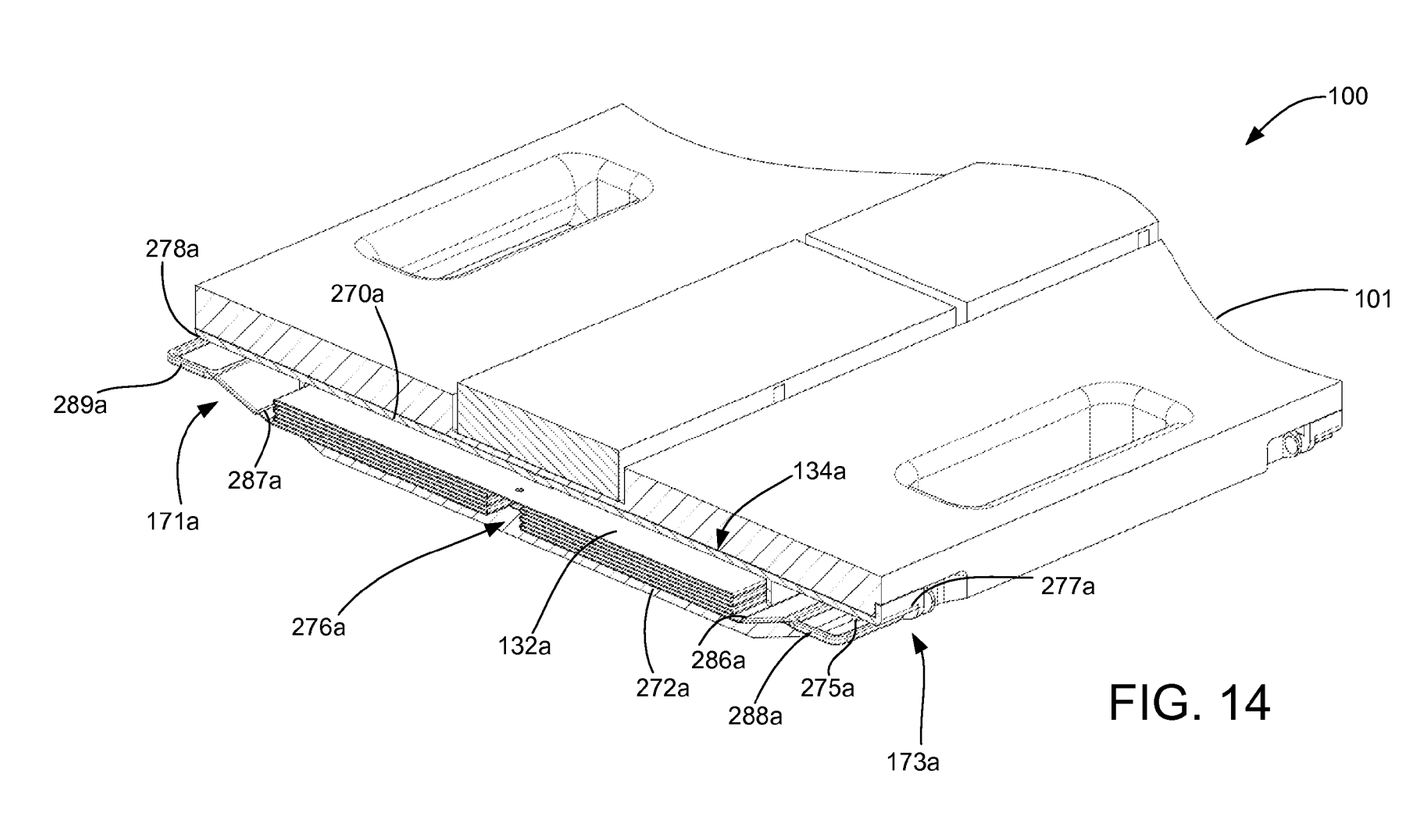
FIG. 14 is a partial perspective view of a section of the spine board illustrating the placement of the exemplary lateral cartridge in the main body of the spine board.

FIG. 14 is a partial perspective view of a section of main body 101 of spine board 100 taken through the line indicated in FIG. 1 and illustrating the exemplary placement of exemplary lateral cartridge 134a in main body 101 of spine board 100. Each lateral cartridge 134a-d further includes a compartment for containing and storing a lateral strap made of hook and loop material. As illustrated in FIGS. 12 and 14, lateral cartridge 134a includes a compartment 276a defined by a top wall 270a, a bottom wall 272a, a first side wall 274a, a second side wall 275a, a trailing end opening 277a located proximal to trailing end 173a and a leading end opening 278a located proximal to leading end 171a. Openings 277a and 278a provide access to lateral strap 132a.

In particular, each lateral strap is stored in each lateral cartridge 134a-d in a dual serpentine arrangement of hook and loop strap material (i.e., a dual arrangement of strap material folded over and onto itself) with the center of each lateral strap secured to the center of the top wall of each lateral cartridge 134a-d so as to prevent the entirety of each lateral strap from exiting from each lateral cartridge 134a-d. In this way, a first end of each lateral strap can exit out a leading end of each lateral cartridge and each second end of each lateral strap can exit out a trailing end of each lateral cartridge. For example, in FIGS. 12 and 14, lateral strap 132a includes first end 286a and second end 287a with equal lengths of strap formed into first and second serpentine arrangements and the center of lateral strap 132a secured to top wall 270a using at least one fastener 285a, such as one more rivets. In addition, each lateral strap located in each lateral cartridge 134a-d includes finger hooks located at their ends. First end 286a of strap 132a includes a first end finger hook 288a and second end 287a of strap 132a includes a second end finger hook 289a. First end finger hook 288a is secured to trailing end 173a of lateral cartridge 134a and second end finger hook 289a is secured to leading end 171a of lateral cartridge 134a when lateral strap 132a is not in use so as to prevent accidental or premature removal of both sides of the strap 132a from cartridge 134a.

As illustrated in FIG. 8, to insert and place lateral cartridges 134a-d in main body 101 of spine board 100, the leading ends 171a-d of lateral cartridges 134a-d are inserted into channels 124a-d, respectively, and are slid from second longitudinal side 112 of main body 101 to first longitudinal side 110 until leading ends 171a-d reach first longitudinal side 110. As lateral cartridges 134a-d reach their full insertion position, the spring or barbed clips on trailing ends 173a-d will become compressed and as insertion is completed the spring or barbed clips will click into position, thereby indexing with main body 101 and holding cartridges 134a-d in place. The spring or barbed clips prevent the lateral cartridges 134a-d from being removed accidentally and additionally keep the lateral cartridges 134a-d in position as straps are removed for use on the patient. Still further, the flanges, such as flanges 280a, 281a and 282a (FIG. 13) provide a hard stop, which prevents cartridges 134a-d from passing completely through main body 101 of board 100.

Each strap contained and stored in each lateral cartridge 134a-d, such as strap 132a, includes a first end that is pulled from the leading end 171a-d and a second end that is pulled from the trailing end 173a-d using the finger hooks on the first and second ends of the straps, such as finger hook 289a located on second end 287a of strap 132a and finger hook 288a located on first end 286a of strap 132a. The straps, made of hook and loop material, are wrapped around the patient and placed on top of themselves or each other to secure the patient's torso, waist and legs to the board. Although unnecessary, it is possible to further thread the straps through the handles by twisting the strap at the handle to allow for hook and loop surfaces to contact each other. All four straps in all four lateral cartridges 134a-d should be utilized to securely fasten the patient to spine board 100. In regards to securing the longitudinal straps in longitudinal cartridges 129a and 129b, the longitudinal straps are brought over the shoulders of the patient, crossed and are attached via its hook and loop material to the lateral straps that were wrapped around the patient. In one embodiment, the load to the longitudinal straps will be divided across multiple lateral straps. If additional strength is required, then the longitudinal straps can be threaded through any of handles 116 to provide further strength.

For sanitation purposes, both longitudinal cartridges 129a-b and lateral cartridges 134a-d including the straps that they house are single use and are removed for replacement. Cartridges 129a-b and 134a-d are easily removed from main body 101 by grasping the spring or barbed clips, such as 183b and 184b and 283a and 284a, and squeezing them toward the center of the respective cartridge while pulling the respective cartridge from main body 101.

Figure 15:
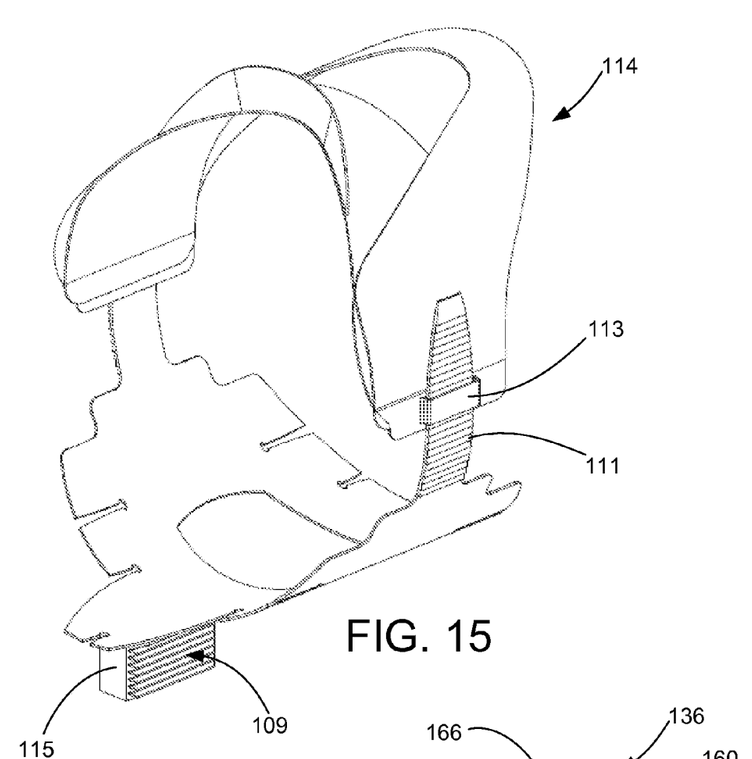
FIG. 15 is a perspective view of a cervical collar according to one embodiment.

FIG. 15 is a perspective view of cervical collar 114. Cervical collar 114 is composed of different density polyethylene plastic materials based on function. Use of polymer-type materials will be apparent to one of skill in the art. A high density polyethylene provides structural strength when surrounding the cervical portion of the spine as well as provides strength for post 115, which is attached to the back of collar 114. A polyethylene foam provides a pad to the contact areas. An ice pack can also pad the contact areas and will provide a therapeutic cooling effect to the cervical area confined to collar 114 (if activated). Collar 114 stores in a low, flat profile and assumes a three-dimensional configuration when wrapped around the patients neck and secured with a pair of saw tooth straps and corresponding buckles. In addition, collar 114 and post 115 are radiolucent to allow x-rays to be taken without removal of the patient from the collar or the spine board. In another embodiment, collar 114 can contain phosphors for radiating visible light after being energized so as to be "glow-in-the-dark." Collar 114 is designed to be slid under the arch of the subject's neck. It is secured to the patient using a saw tooth strap 111 and buckle 113 configuration and secured to main body 101 of board 100 using post 115 that has exterior facing grooves or indexing slots 109. It should be realized that other ways to secure collar to a patient's neck are possible. In another embodiment, cervical collar 114 has multiple distal contact points including, but not limited to contact points with the bilateral clavicles, bilateral trapezius muscles, the sternum, posterior soft tissues overlying the occiput and anteriorly the mandible and its soft tissue.

Figure 16:
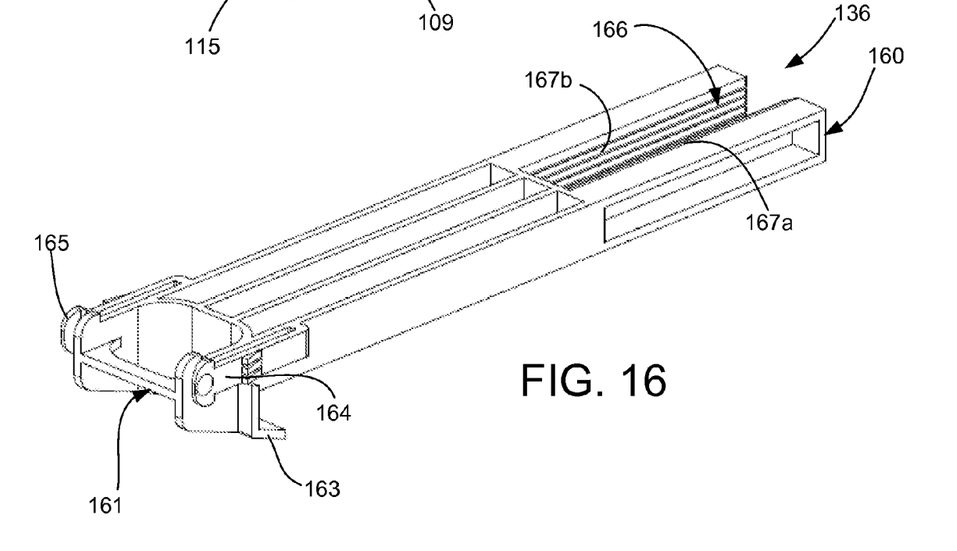
FIG. 16 is a perspective view of a collar stabilization key for securing the cervical collar of FIG. 15 to the spine board according to one embodiment.

As previously discussed, cervical collar 114 contains at least two features: a chemically activated cold pack embedded within the collar that can be activated by medical personnel if the situation calls for it, and supporting post 115 that can be inserted into an opening 117 in main body 101 of board 100 and locked into place with collar stabilization key 136. FIG. 16 is a perspective view of collar stabilization key 136. Collar stabilization key 136 includes a leading end 160 and a trailing end 161. Trailing end 161 includes a flange 163 that is for engaging with main body 101 of board 100. Trailing end 161 also includes a pair of spring or barbed clips 164 and 165. Extending from leading end 161 and less than halfway to trailing end 161 is a passage 166 having interior facing sides with grooves or indexing slots 167*a* and 167*b* that face each other. Indexing slots 167*a* and 167*b* are for engaging with the grooves or indexing slots 109 on either side of the exterior facing surfaces of post 115. Providing post 115 with varying heights of indexing slots 109 and collar stabilization key 136 with varying heights of indexing slots 167*a* and 167*b* allow for the patient's head to be positioned above top surface 102 of board 100 should it be required.

Figure 17:
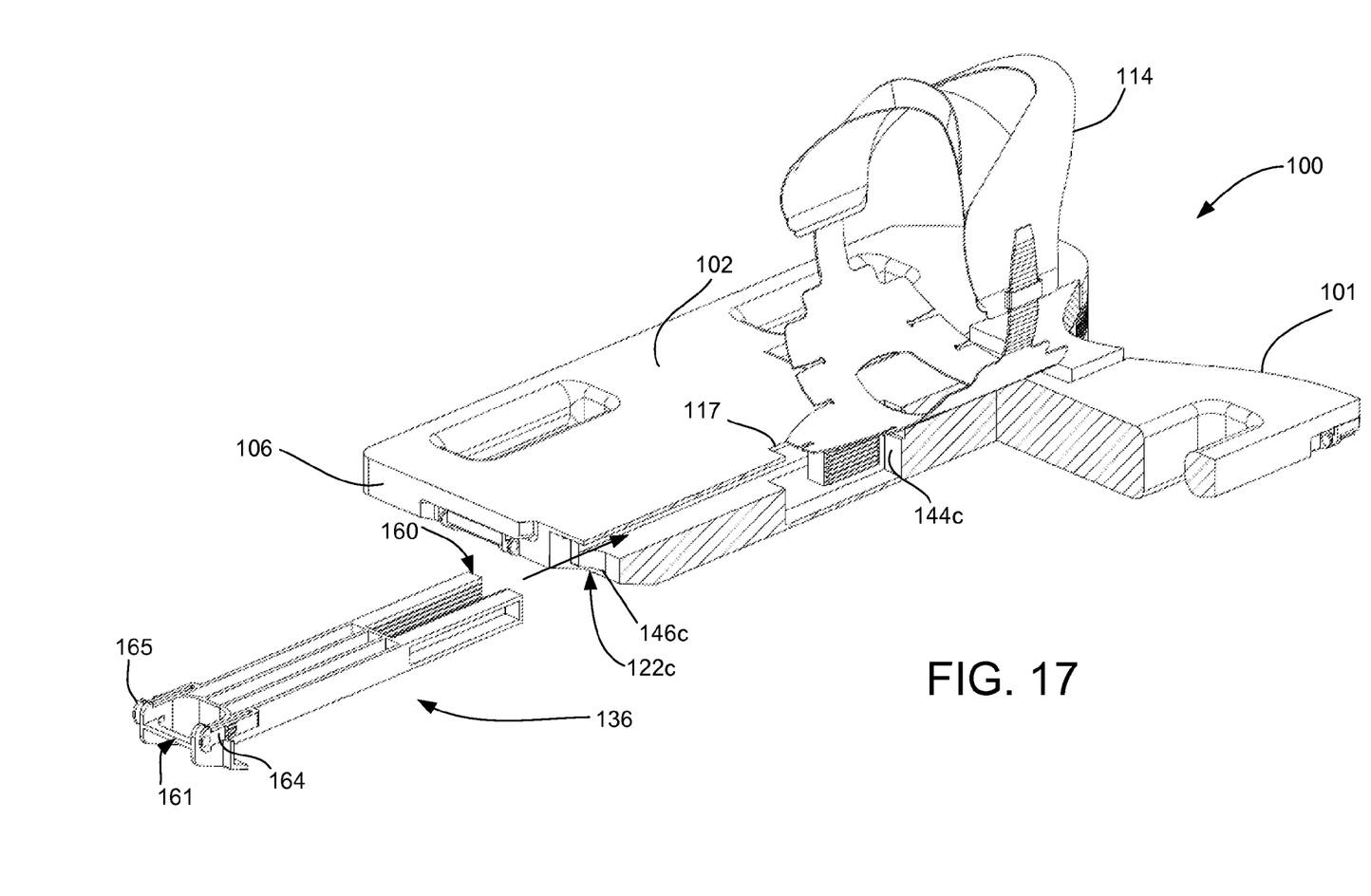
FIG. 17 is a partial perspective view of a section of the spine board illustrating the insertion of and placement of the collar stabilization key in the spine board.

FIG. 17 is a partial perspective view of a section of spine board 100 illustrating the insertion of and placement of collar stabilization key 136 in main body 101 of spine board 100. As illustrated, the leading end 160 of collar stabilization key 136 is inserted into a third longitudinal channel 122*c* in the direction illustrated by the directional arrows. Third longitudinal channel 122*c* includes a first end 144*c* and a second end 146*c* and is located between first and second longitudinal channels 122*a* and 122*b*. Second end 146*c* intersects with first end 106 of main body 101. Collar stabilization key 136 is slid into third longitudinal channels 122*c* in the direction illustrated by the directional arrow until leading end 160 reaches first end 144*c* of channel 122*c* where post 115 is inserted through an opening 117 in top surface 102 of main body 101. As collar stabilization key 136 reaches its full insertion position, the spring or barbed clips 164 and 165 on trailing end 161 will become compressed and as insertion is completed the spring or barbed clips 164 and 165 will click into position, thereby indexing with main body 101 and holding collar stabilization key 136 in place as well as post 115, which prevents any motion of the patient's neck (either lateral translation and rotation) during transportation. The spring or barbed clips also prevent collar stabilization key 136 from being removed accidentally. Collar stabilization key 136 can be easily removed from main body 101 by grasping spring or barbed clips 163 and 164 and squeezing them toward the center of collar stabilization key 136 while pulling the collar stabilization key 136 from longitudinal channel 122*c* of main body 101.

Although elements have been shown or described as separate embodiments above, portions of each embodiment may be combined with all or part of other embodiments described above.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A spine board comprising:
   a main body having:
      a top surface and an opposing bottom surface that define a thickness of the main body;
      a first end and an opposing second end that define a length of the main body;
      a first longitudinal side and an opposing second longitudinal side that define a width of the main body, wherein the first and second longitudinal sides connect the first end to the second end;
   a longitudinal channel extending longitudinally within the main body, wherein the longitudinal channel is defined at least by an open first end and an open second end, wherein the open first end intersects with the first end of the main body and the open second end intersects with the top surface of the main body; and
   a collar stabilization key having a leading end, a trailing end and is received by the longitudinal channel, the leading end of the collar stabilization key mates with a post that is inserted through the open second end of the longitudinal channel and couples to a cervical collar so as to secure the cervical collar to the main body of the spine board.

2. The spine board of claim 1, wherein the trailing end of the collar stabilization key locks the collar stabilization key in the longitudinal channel.

3. The spine board of claim 1, further comprising:
   a plurality of lateral channels extending laterally within the main body and being defined at least by an open first end and an open second end, wherein the open first end intersects with the first longitudinal side of the main body and the open second end intersects with the second longitudinal side of the main body; and
   a plurality of lateral cartridges each containing a lateral strap and is removably inserted into one of the plurality of lateral channels, wherein the lateral cartridges each have a leading end that is located at the open first end of the lateral channels and a trailing end that is located at the open second ends of the lateral channels.

4. The spine board of claim 3, wherein the plurality of lateral channels are spaced apart from the top surface and the bottom surface and are oriented substantially perpendicular to the longitudinal channel.

5. A spine board comprising:
   a main body having:
      a top surface and an opposing bottom surface that define a thickness of the main body;
      a first end and an opposing second end that define a length of the main body;
      a first longitudinal side and an opposing second longitudinal side that define a width of the main body, wherein the first and second longitudinal sides connect the first end to the second end;
   a plurality of lateral channels extending laterally within the main body and being defined at least by open first ends and open second ends, wherein each open first end intersects with the first longitudinal side of the main body and each open second end intersects with the second longitudinal side of the main body;
   a plurality of lateral cartridges each being removably inserted into one of the plurality of lateral channels; and
   a plurality of lateral straps each contained in one of the plurality of lateral cartridges so that at least a portion of each lateral strap is fixed inside the main body and a portion of each lateral strap is used to secure a patient to the top surface of the main body.

6. The spine board of claim 5, wherein each of the plurality of lateral channels comprises a length that is the width of the main body.

7. The spine board of claim 5, wherein each of the plurality of lateral cartridges has a leading end that is located at the open first ends of the lateral channels when placed in the lateral channels and a trailing end that is located at the open second ends of the lateral channels when placed in the lateral channels, the trailing end locking the lateral cartridge to the main body.

8. The spine board of claim 7, wherein each lateral strap is folded over on top of itself in two places so that a first end of each lateral strap exits out the leading end of each lateral cartridge and a second end of each lateral strap exits out the trailing end of each lateral cartridge.

9. The spine board of claim 8, wherein the first end of each lateral strap includes a finger hook that is secured to an interior wall of the leading end of each lateral cartridge when not in use and wherein the second end of each lateral strap includes a finger hook that is secured to an interior wall of the trailing end of each lateral cartridge when not in use.

10. The spine board of claim 5, wherein the plurality of lateral channels are spaced apart from the top surface and the bottom surface of the main body and from each other along the length of the main body.

11. The spine board of claim 5, wherein each end of each lateral strap comprises hook and loop material, and is configured to wrap over a torso, waist and legs of the patient respectively.

12. The spine board of claim 5, further comprising a collar stabilization key having a leading end and a trailing end and is inserted into a longitudinal channel having a first end that intersects with the first end of the main body and a second end that intersects with the top surface of the main body, the leading end of the collar stabilization key mates with a post coupled to a cervical collar so as to secure the cervical collar to the main body of the spine board and the trailing end of the collar stabilization key locks the collar stabilization key in the longitudinal channel.

13. A method of securing a patient to a spine board, the method comprising:
  providing a main body of the spine board having:
    a top surface and an opposing bottom surface defining a thickness of the main body;
    a first end and an opposing second end defining a length of the main body;
    a first longitudinal side and a second longitudinal side defining a width of the main body;
  pulling a lateral strap from a lateral cartridge located in a lateral channel in the main body, wherein the lateral channel is located between the top and bottom surfaces, extends laterally for less than the length of the main body and has an open first end and an open second end; and
  securing the lateral strap over a patient using hook and loop material that comprises the lateral strap.

14. A spine board comprising:
  a main body of the spine board having:
    a top surface and an opposing bottom surface defining a thickness of the main body;
    a first end and an opposing second end defining a length of the main body;
    a first longitudinal side and a second longitudinal side defining a width of the main body;
  a lateral strap housed in a lateral cartridge located in a lateral channel in the main body, wherein the lateral channel is located between the top and bottom surfaces, extends laterally between the first and second longitudinal sides of the main body and has an open first end and an open second end; and
  wherein the lateral strap is configured for securing over a patient using hook and loop material that comprises the lateral strap.

15. The spine board of claim 14, further comprising a longitudinal channel having a first end that intersects with the first end of the main body and a second end that intersects with the top surface of the main body.

16. The spine board of claim 15, further comprising a collar stabilization key having a leading end and a trailing end and being inserted into the longitudinal channel.

17. The spine board of claim 16, wherein the leading end of the collar stabilization key mates with a post coupled to a cervical collar so as to secure the cervical collar to the main body of the spine board and the trailing end of the collar stabilization key locks the collar stabilization key in the longitudinal channel.

* * * * *